(12) United States Patent
Cavalla et al.

(10) Patent No.: US 6,211,367 B1
(45) Date of Patent: Apr. 3, 2001

(54) METHODS OF SYNTHESING PURINE COMPOUNDS HAVING PDE IV INHIBITORY ACTIVITY

(75) Inventors: David J. Cavalla, Cambridge (GB); Mark Chasin, Manalapan, NJ (US); Peter Hofer, Liestal (CH)

(73) Assignee: Euro-Celtique, S.A., Luxemburg (LU)

( * ) Notice: Subject to any disclaimer, the term of this patent is extended or adjusted under 35 U.S.C. 154(b) by 0 days.

(21) Appl. No.: 09/210,557

(22) Filed: Dec. 11, 1998

Related U.S. Application Data

(60) Provisional application No. 60/069,371, filed on Dec. 12, 1997.

(51) Int. Cl.[7] ............ C07D 473/34; C07D 487/04; C07D 471/04; A61K 31/52; A61P 11/06
(52) U.S. Cl. ............ 544/277; 544/180; 544/236; 546/118
(58) Field of Search ............ 544/277; 514/263

(56) References Cited

PUBLICATIONS

Some New N–Methylpurines, Gertrude B. Elion, CIBA foundation Symp. Chem. Biol. Purines, 1957, pp. 39–49.
Selective Type IV Phosphodiesterase Inhibitors as Antiasthmatic Agents. The Syntheses and Biological Activities of 3–(Cyclopentyloxy)–4–methoxybenzamides and Analogues, Michael J. Ashton, et al., Journal of Medicinal Chemistry, 1994, vol. 37, No. 11, pp. 1696–1703.
Synthesis of 3–Methylisoguanine [6–Amino–3–methylpurin–2(3H)–one], G.T. Rogers and T.L. B. Ulbricht, J. Chemical Soc. (C), 1971, pp. 2364–2366.
Synthesis of Potential Anticancer Agents. XIX. 2–Substituted N[6]–Alkyladenines, John A. Montgomery, Lee B. Holum and Thomas P. Johnston The Kettering–Meyer Laboratory, Southern Research Institute, Aug. 5, 1959, vol. S. pp. 3963–3967.
The photosolvolysis of N–arylmethyladenines. Photoremovable N–arylmethyl protective groups for N–containing compounds., A. Er–Rhaimini, et al., Tetrahedron Letters, vol. 31, No. 40, pp. 5757–5760, 1990.
Heterocyclic Ambident Nucleophiles. IV* The Alkylation of Metal Salts of Adenine, Malcolm Rasmussen, et al., Aust. J. Chem., 1982, 35, 535–42.

Primary Examiner—Mark L. Berch
(74) Attorney, Agent, or Firm—Davidson, Davidson & Kappel LLC

(57) ABSTRACT

The present invention comprises compounds having the general formula I:

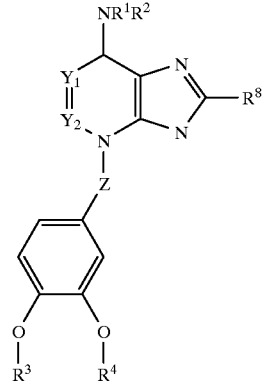

(I)

wherein:
  Y, is N or CH
  Z is selected from the group consisting of alkyl groups such as alkylene groups such as $CH_2$, $CH_2CH_2$, $CH(CH_3)$; alkenyl groups such as $CH=CH$; alkynyl groups such as $C\equiv C$; and NH, $N(C_1-C_3$ alkyl), O, S, $C(O)CH_2$ and $OCH_2$;
  $R^1$ and $R^2$ are selected from the group consisting of hydrogen and a $C_1-C_8$ straight or branched alkyl or a $C_3-C_8$ cycloalkyl;
  $R^3$ is a $C_3-C_{12}$ straight or branched alkyl;
  $R^4$ is a $C_3-C_{10}$ cycloalkyl optionally substituted with OH or $C_3-C_{10}$ cycloalkenyl optionally substituted with OH; and
  $R^8$ is a $C_1-C_8$ straight or branched alkyl or a $C_3-C_8$ cycloalkyl, optionally substituted with OH;
and methods of synthesis.

12 Claims, No Drawings

METHODS OF SYNTHESING PURINE COMPOUNDS HAVING PDE IV INHIBITORY ACTIVITY

This application claims priority from of provisional application Ser. No. 60/069,371, filed Dec. 12, 1997.

BACKGROUND OF THE INVENTION

Asthma is a complex disease involving the concerted actions of multiple inflammatory and immune cells, spasmogens, inflammatory mediators, cytolines and growth factors. In recent practice there have been four major classes of compounds used in the treatment of asthma, namely bronchodilators (e.g., β-adrenoceptor agonists), antiinflammatory agents (e.g., corticosteroids), prophylactic anti-allergic agents (e.g., cromolyn sodium) and xanthines (e.g., theophylline) which appear to possess both bronchodilating and anti-inflammatory activity.

Theophylline has been a preferred drug of first choice in the treatment of asthma. Although it has been touted for its direct bronchodilatory action, theophylline's therapeutic value is now believed to also stem from anti-inflammatory activity. Its mechanism of action remains unclear. However, it is believed that several of its cellular activities are important in its activity as an anti-asthmatic, including cyclic nucleotide phosphodiesterase inhibition, adenosine receptor antagonism, stimulation of catecholamine release, and its ability to increase the number and activity of suppressor T-lymphocytes. While all of these may actually contribute to its activity, only PDE inhibition may account for both the antiinflammatory and bronchodilatory components. However, theophylline is known to have a narrow therapeutic index and a wide range of untoward side effects which are considered problematic.

Of the activities mentioned above, theophylline's activity in inhibiting cyclic nucleotide phosphodiesterase has received considerable attention recently. Cyclic nucleotide phosphodiesterases (PDEs) have received considerable attention as molecular targets for anti-asthmatic agents. Cyclic 3',5'-adenosine monophosphate (cAMP) and cyclic 3',5'-guanosine monophosphate (cGMP) are known second messengers that mediate the functional responses of cells to a multitude of hormones, neurotransmitters and autocoids. At least two therapeutically important effects could result from phosphodiesterase inhibition, and the consequent rise in intracellular adenosine 3',5'-monophosphate (cAMP) or guanosine 3',5'-monophosphate (cGMP) in key cells in the pathophysiology of asthma. These are smooth muscle relaxation (resulting in bronchodilation) and anti-inflammatory activity.

It has become known that there are multiple, distinct PDE isoenzymes which differ in their cellular distribution. A variety of inhibitors possessing a marked degree of selectivity for one isoenzyme or the other have been synthesized.

The structure-activity relationships (SAR) of isozyme-selective inhibitors has been discussed in detail, e.g., in the article of Theodore J. Torphy, et al., "Novel Phosphodiesterase Inhibitors For The Therapy Of Asthma", Drug News & Prospectives, 6(4) May 1993, pages 203–214. The PDE enzymes can be grouped into five families according to their specificity toward hydrolysis of cAMP or cGMP, their sensitivity to regulation by calcium, calmodulin or cGMP, and their selective inhibition by various compounds. PDE I is stimulated by $Ca^{2+}$/calmodulin. PDE H is cGMP-stimulated, and is found in the heart and adrenals. PDE III is cGNT-inhibited, and inhibition of this enzyme creates positive inotropic activity. PDE IV is cAMP specific, and its inhibition causes airway relaxation, antiinflammatory and antidepressant activity. PDE V appears to be important in regulating cGMP content in vascular smooth muscle, and therefore PDE V inhibitors may have cardiovascular activity.

While there are compounds derived from numerous structure activity relationship studies which provide PDE III inhibition, the number of structural classes of PDE IV inhibitors is relatively limited. Analogues of rolipram, which has the following structural formula (A):

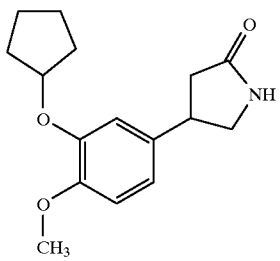

and of RO-20-1724, which has the following structural formula (B):

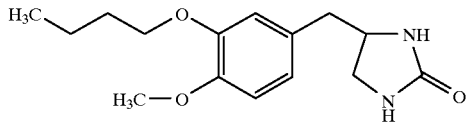

have been studied.

U.S. Pat. No. 4,308,278 discloses compounds of the formula (C)

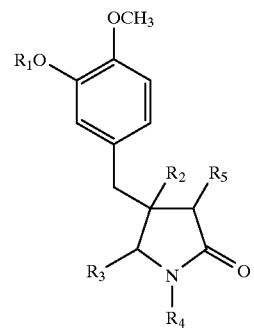

wherein $R_1$ is ($C_3$–Cd cycloalkyl or benzyl; each of R and $R_3$ is hydrogen or ($C_1$–$C_4$) alkyl; $R_4$ is $R_2$ or alkoxycarbonyl; and $R_5$ is hydrogen or alkoxycarbonyl.

Compounds of Formula (D) are disclosed in U.S. Pat. No. 3,636,039. These compounds are benzylimidazolidinones which act as hypertensive agents.

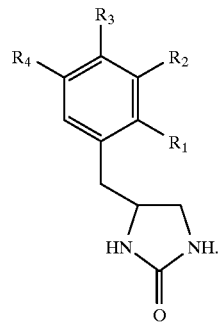

Substituents R$_1$–R$_4$ in Formula D represent a variety of groups, including hydrogen and lower alkyl.

PCT publication WO 87/06576 discloses antidepressants of Formula E:

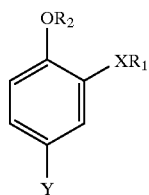

wherein R$_1$ is a polycycloalkyl group having from 7 to 11 carbon atoms; R$_2$ is methyl or ethyl; X is O or NH; and Y comprises a mono- or bicyclic heterocyclic group with optional substituents.

Rolipram, which was initially studied because of its activity as an antidepressant, has been shown to selectively inhibit the PDE IV enzyme and this compound has since become a standard agent in the classification of PDE enzyme subtypes. There appears to be considerable therapeutic potential for PDE IV inhibitors. Early work focused on depression as a CNS therapeutic endpoint and on inflammation, and has subsequently been extended to include related diseases such as dementia, including vascular dementia, multi-in-farct dementia and Alzheimer's Disease, and asthma In-vitro, rolipram, RO20-1724 and other PDE IV inhibitors have been shown to inhibit (1) mediator synthesis/release in mast cells, basophils, monocytes and eosinophils; (2) respiratory burst, chemotaxis and degranulation in neutrophils and eosinophils; and (3) mitogen-dependent growth and differentiation in lymphocytes (The PDE IV Family Of Calcium-Phosphodiesterases Enzymes, John A. Lowe, III, et al., Drugs of the Future 1992, 17(9):799–807).

PDE IV is present in all the major inflammatory cells in asthma including eosinophils, neutrophils, T-lymphocytes, macrophages and endothelial cells. Its inhibition causes down regulation of inflammatory cell activation and relaxes smooth muscle cells in the trachea and bronchus. On the other hand, inhibition of PDE III, which is present in myocardium, causes an increase in both the force and rate of cardiac contractility. These are undesirable side effects for an anti-inflammatory agent. Theophylline, a non-selective PDE inhibitor, inhibits both PDE III and PDE IV, resulting in both desirable anti-asthmatic effects and undesirable cardiovascular stimulation. With this well-known distinction between PDE isozymes, the opportunity for concomitant anti-inflammation and bronchodilation without many of the side effects associated with theophylline therapy is apparent.

The increased incidence of morbidity and mortality due to asthma in many Western countries over the last decade has focused the clinical emphasis on the inflammatory nature of this disease and the benefit of inhaled steroids. Development of an agent that possesses both bronchodilatory and antiinflammatory properties would be most advantageous.

It appears that selective PDE IV inhibitors should be more effective with fewer side effects than theophylline. Clinical support has been shown for this hypothesis. Furthermore, it would be desirable to provide PDE IV inhibitors which are more potent and selective than rolipram and therefore have a lower IC$_{50}$ so as to reduce the amount of the agent required to effect PDE IV inhibition.

In recent years, several different compounds have been suggested as possible therapeutic compositions which achieve the desired PDE IV inhibition without the side effects alluded to above. However, these efforts have been chiefly directed to developing non-specific derivatives of particular classes of compounds, i.e. rolipram analogs, benzoxazoles, adenines, thioxanthines, etc. These efforts, however, have resulted in a myriad of compounds having a wide range of PDE IV IC$_{50}$'s. Often, the general formulas disclosed yield several compounds which have poor levels of PDE IV inhibition and/or lack sufficient specificity. Consequently, these efforts often provide no assurance that any particular derivative within the formula will have the desired combination of high PDE IV inhibition and selectivity.

It has now been discovered that a variety of fused heterocyclic ring structures having a 3-cyclopentyloxy-4-methoxybenzyl substituent show PDE IV inhibitory activity.

OBJECT AND SUMMARY OF THE INVENTION

It is accordingly a primary object of the present invention to provide new compounds which are more effective selective PDE IV inhibitors than known prior art compounds.

It is another object of the present invention to provide new compounds which act as effective PDE IV inhibitors with lower PDE m inhibition.

It is another object of the present invention to provide methods for treating a patient requiring PDE IV inhibition.

It is another object of the present invention to provide new compounds for treating disease states associated with abnormally high physiological levels of inflammatory cytokines, including tumor necrosis factor.

It is another object of the present invention to provide a method of synthesizing the new compounds of this invention.

It is another object of the present invention to provide a method for treating a patient suffering from disease states such as asthma, allergies, inflammation, depression, dementia, including vascular dementia, multi-in-farct dementia, and Alzheimer's Disease, a disease caused by Human Immunodeficiency Virus and disease states associated with abnormally high physiological levels of inflammatory cytokines.

Other objects and advantages of the present invention will become apparent from the following detailed description thereof.

With the above and other objects in view, the present invention comprises compounds having the general formula I:

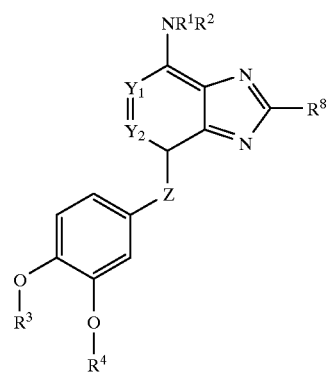

wherein:
Y$_1$ and Y$_2$ are independently selected from the group consisting of N or CH;

Z is selected from the group consisting of alkylene groups such as $CH_2$, $CH_2CH_2$, $CH(CH_3)$; alkenylene groups such as $CH=CH$; alkynylene groups such as $C\equiv C$; and NH, $N(C_1-C_3$ alkyl), O, S, $C(O)CH_2$ and $OCH_2$;

$R^1$ and $R^2$ are independently selected from the group consisting of hydrogen and a $C_1-C_8$ straight or branched alkyl or $C_3-C_8$ cycloalkyl;

$R^3$ is a $C_1-C_{12}$ straight or branched alkyl;

$R^4$ is a $C_3-C_{10}$ cycloalkyl optionally substituted with OH, or a $C_3-C_{10}$ cycloalkenyl optionally substituted with OH, and $R^8$ is a $C_1-C_8$ straight or branched alkyl or a $C_3-C_8$ cycloalkyl, optionally substituted with OH.

The present invention is also related to methods of using compounds of formula I for treating patients who can benefit from a modification of PDE IV enzyme activities in their bodies.

The invention also comprises methods of making compounds of formula L according to a synthetic scheme as generally set forth in Schemes 1, 2, 3 and 4. The stated conditions in these schemes are includes as examples only, and are not meant to be limiting in any manner.

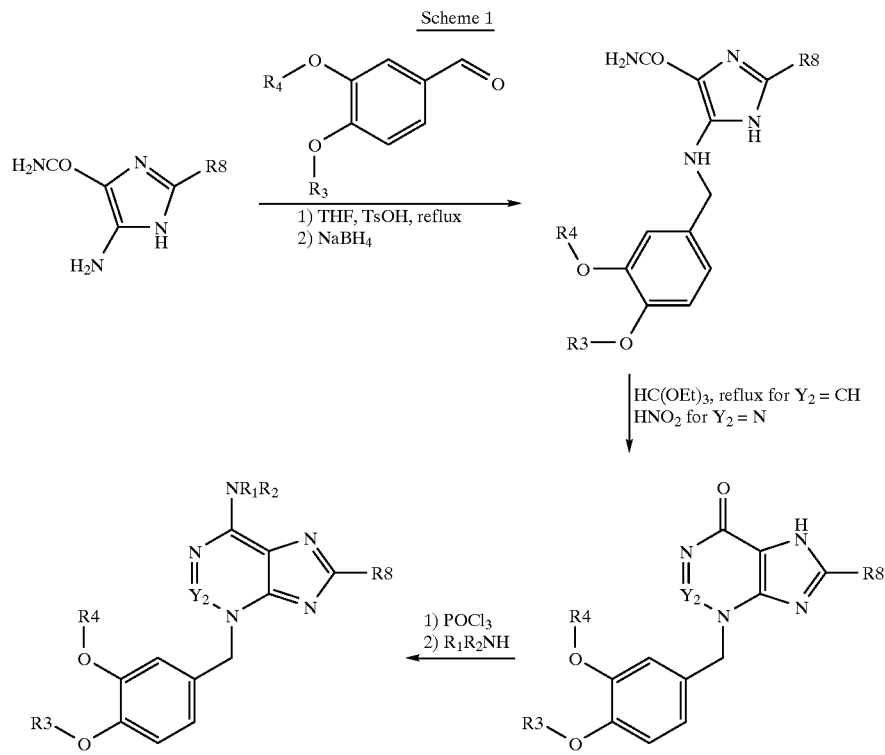

-continued
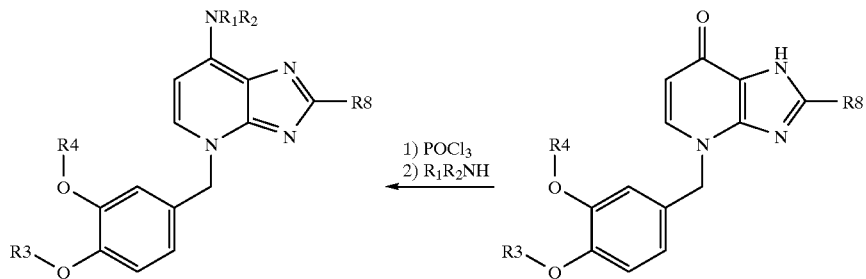
Scheme 3
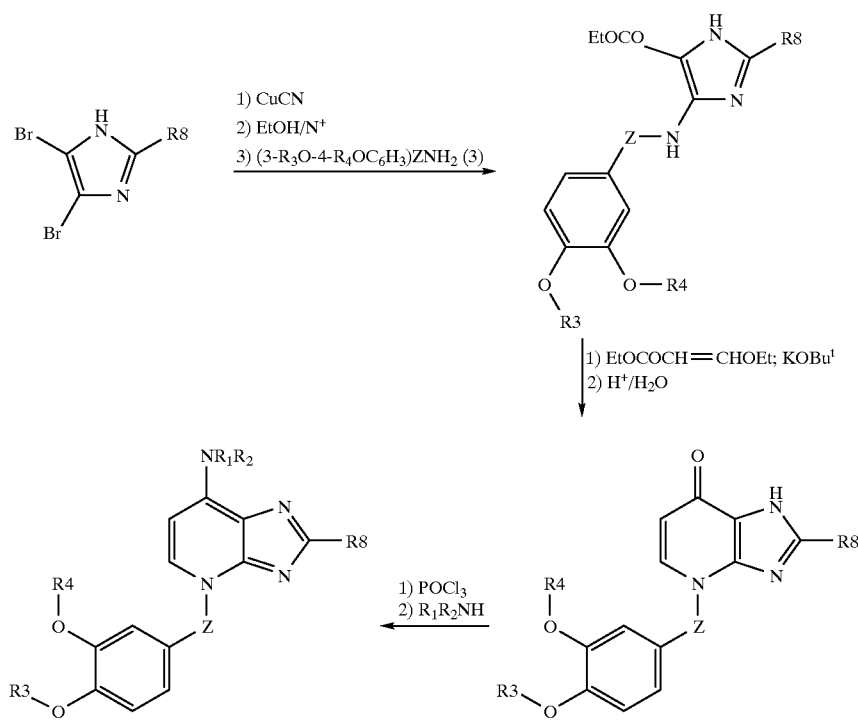
Scheme 4
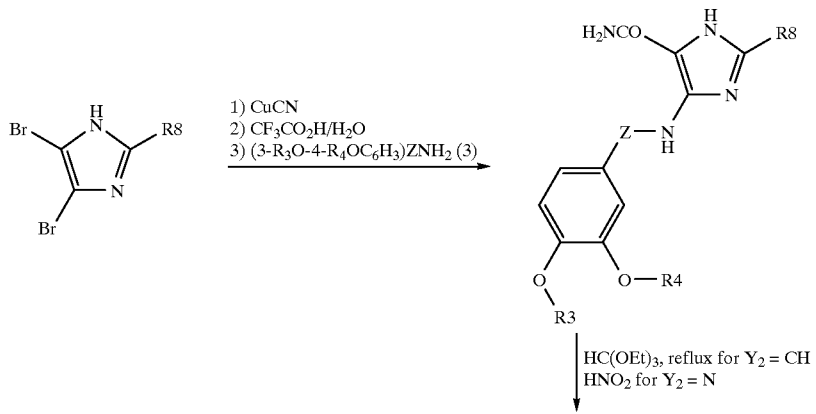

-continued

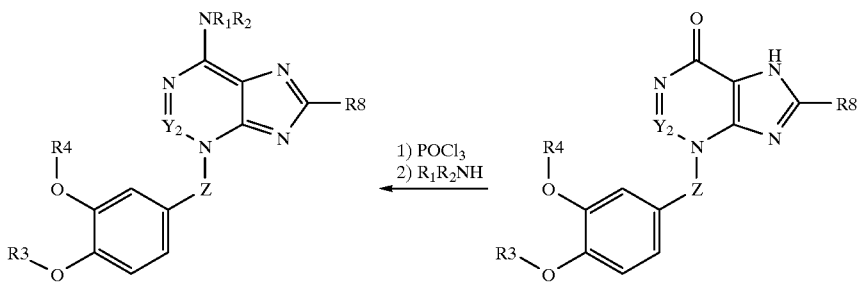

The invention is also related to a method of treating mammals with the above compounds.

DETAILED DESCRIPTION OF THE INVENTION

The present invention is directed to compounds having the general formula I:

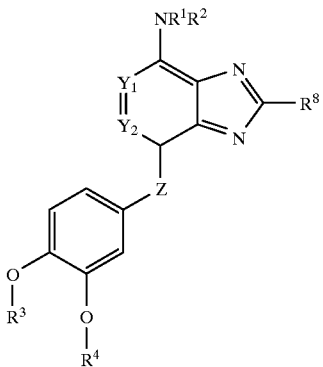

wherein:
  $Y_1$ and $Y_2$ are independently selected from the group consisting of N or CH;
  Z is selected from the group consisting of alkylene groups such as $CH_2CH_2CH_2$, $CH(CH_3)$, alkenylene groups such as $CH=CH$; alkynylene groups such as $C\equiv C$; and NC, $N(C_1-C_3$ alkyl), O, S, $C(O)CH_2$ and $OCH_2$;
  $R^1$ and $R^2$ are independently selected from the group consisting of hydrogen and a $C_1-C_8$ straight or branched alkyl or $C_3-C_8$ cycloalkyl;
  $R^3$ is a $C_1-C_{12}$ straight or branched alkyl;
  $R^4$ is a $C_3-C_{10}$ cycloalkyl optionally substituted with OH, or a $C_3-C_{10}$ cylcoalkenyl optionally substituted with OH; and
  $R^8$ is a $C_1-C_8$ straight or branched alkyl or a $C_3-C_8$ cycloalkyl, optionally substituted with OH.

As used herein, the following terms are intended to have the meaning as understood by persons of ordinary skill in the art, and are specifically intended to include the meanings set forth below:

"Alkyl" means a linear or branched aliphatic hydrocarbon group having a single radical. Examples of alkyl groups include methyl, propyl, isopropyl, butyl, n-butyl, isobutyl, sec-butyl, tert-butyl, pentyl, hexyl, heptyl, cetyl, and the like. A branched alkyl means that one or more alkyl groups such as methyl, ethyl or propyl are attached to a linear alkyl chain.

The term "cycloalkyl" means a non-aromatic mono- or multicyclic ring system having a single radical. Exemplary monocyclic cycloalkyl rings include cyclopentyl, cyclohexyl and cycloheptyl. Exemplary multicylic cycloalkyl rings include adamantyl and norbornyl.

The term "cycloalkenyl" means a non-aromatic monocyclic or multicyclic ring system containing a carbon-carbon double bond and having a single radical. Exemplary monocyclic cycloalkenyl rings include cyclopentenyl, cyclohexenyl or cycloheptenyl. An exemplary multicyclic cycloalkenyl ring is norbornenyl.

"Alkylene" means a linear or branched aliphatic hydrocarbon group having two radicals. Examples of alkylene groups include methylene, propylene, isopropylene, butylene, and the like.

The term "alkenylene" means a linear or branched aliphatic hydrocarbon group containing a carbon-carbon double bond, having two radicals.

The term "alkynylene" means a linear or branched aliphatic hydrocarbon group containing a carbon-carbon triple bond and, having two radicals.

"Alkoxy" means an alkyl-O-group in which the alkyl group is as previously described. Exemplary alkoxy groups include methoxy, ethoxy, n-propoxy, i-propoxy, n-butoxy and heptoxy.

The term "cycloalkoxy" means a cycloalkyl-O-group in which the cycloalkyl group is as previously described. Exemplary cycloalkoxy groups include cyclopentyloxy.

As used herein, the term "patient" includes both human and other mammals.

The present invention also includes organic and inorganic salts, hydrates, esters, prodrugs and metabolites of the compounds of formula I.

The compounds of the present invention can be administered to anyone requiring PDE IV inhibition. Administration may be orally, topically, by suppository, inhalation or insufflation, or parenterally.

The present invention also encompasses all pharmaceutically acceptable salts of the foregoing compounds. One skilled in the art will recognize that acid addition salts of the presently claimed compounds may be prepared by reaction of the compounds with the appropriate acid via a variety of known methods. Alternatively, alkali and alkaline earth metal salts are prepared by reaction of the compounds of the invention with the appropriate base via a variety of known methods. For example, the sodium salt of the compounds of the invention can be prepared via reacting the compound with sodium hydride.

Various oral dosage forms can be used, including such solid forms as tablets, gelcaps, capsules, caplets, granules, lozenges and bulk powders and liquid forms such as emulsions, solutions and suspensions. The compounds of the present invention can be administered alone or can be combined with various pharmaceutically acceptable carriers and excipients known to those skilled in the art, including but not limited to diluents, suspending agents, solubilizers, binders, retardants, disintegrants, preservatives, coloring agents, lubricants and the like.

When the compounds of the present invention are incorporated into oral tablets, such tablets can be compressed, tablet triturates, enteric-coated, sugar-coated, film-coated, multiply compressed or multiply layered. Liquid oral dosage forms include aqueous and nonaqueous solutions, emulsions, suspensions, and solutions and/or suspensions reconstituted from non-effervescent granules, containing suitable solvents, preservatives, emulsifying agents, suspending agents, diluents, sweeteners, coloring agents, and flavorings agents. When the compounds of the present invention are to be injected parenterally, they may be, e.g., in the form of an isotonic sterile solution. Alternatively, when the compounds of the present invention are to be inhaled, they may be formulated into a dry aerosol or may be formulated into an aqueous or partially aqueous solution.

In addition, when the compounds of the present invention are incorporated into oral dosage forms, it is contemplated that such dosage forms may provide an immediate release of the compound in the gastrointestinal tract, or alternatively may provide a controlled and/or sustained release through the gastrointestinal tract. A wide variety of controlled and/or sustained release formulations are well known to those skilled in the art, and are contemplated for use in connection with the formulations of the present invention. The controlled and/or sustained release may be provided by, e.g., a coating on the oral dosage form or by incorporating the compound(s) of the invention into a controlled and/or sustained release matrix.

Specific examples of pharmaceutically acceptable carriers and excipients that may be used to formulate oral dosage forms, are described in the *Handbook of Pharmaceutical Excipients,* American Pharmaceutical Association (1986), incorporated by reference herein. Techniques and compositions for making solid oral dosage forms are described in *Pharmaceutical Dosage Forms: Tablets* (Lieberman, Lachman and Schwartz, editors) 2nd edition, published by Marcel Dekker, Inc., incorporated by reference herein. Techniques and compositions for making tablets (compressed and molded), capsules (hard and soft gelatin) and pills are also described in *Remington's Pharmaceutical Sciences* (Arthur Osol, editor), 1553–1593 (1980), incorporated herein by reference. Techniques and composition for making liquid oral dosage forms are described in *Pharmaceutical Dosage Form, Disperse System,* (Lieberman, Rieger and Banker, editors) published by Marcel Dekker, Inc., incorporated herein by reference.

When the compounds of the present invention are incorporated for parenteral administration by injection (e.g., continuous infusion or bolus injection), the formulation for parenteral administration may be in the form of suspensions, solutions, emulsions in oily or aqueous vehicles, and such formulations may further comprise pharmaceutically necessary additives such as stabilizing agents, suspending agents, dispersing agents, and the like. The compounds of the invention may also be in the form of a powder for reconstitution as an injectable formulation.

The dose of the compounds of the present invention is dependent upon the affliction to be treated, the severity of the symptoms, the route of administration, the frequency of the dosage interval, the presence of any deleterious side-effects, and the particular compound utilized, among other things.

DETAILED DESCRIPTION OF PREFERRED EMBODIMENTS

As used herein, the term "Et" refers to any ethyl group, and the term "Bu" refers to a butyl group. "Bu$^t$" refers to a tertiary butyl group. The term "THF" refers to tetrohydrofuran. The term "DMAC" refers to dimethyl acetate. The term "Ph" refers to a phenyl group. The terms Z; $Y_1$; $Y_2$; $R^1$; $R^2$; $R^3$; $R^4$; and $R^8$ refer to the terms as defined in this application.

The synthetic pathway described in Scheme 1 for producing xanthine compounds of Figure I, wherein Z is $CH_2$ and Y, is N, is described as follows:

Step (a) of the synthetic scheme, compound (II) is subjected to reductive amination using a 2-step procedure employing the benzaldehyde of compound (III) in the presence of an acid, followed by reduction with a reducing agent to yield compound (IV) as shown below:

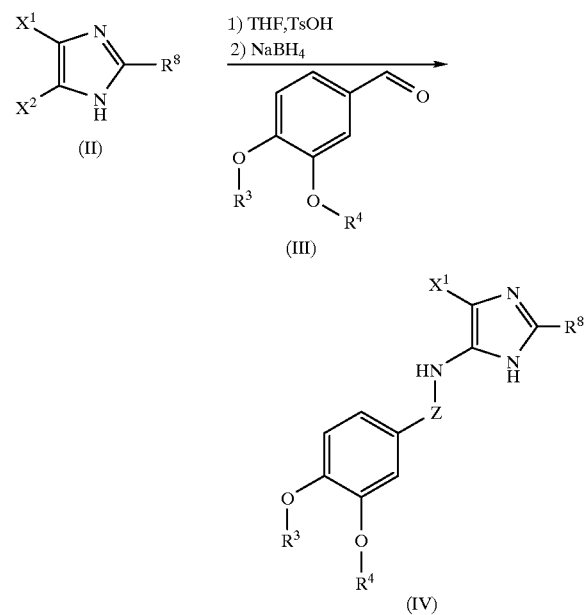

wherein $X^1$ is a carboxamide, $X^2$ is an amino group and Z is $CH_2$. The acid of this step can be any suitable acid, e.g. tosic acid or p-toluenesulfonic acid. Any suitable reducing agent can be used in this step, e.g. a borane anion such as sodium borohydride. The reaction of step (a) can occur in a suitable solvent e.g. methanol or THF.

Step (i) of the reaction involves cyclizaton of compound (I)to form the hypoxanthine of compound (V) as set forth below:

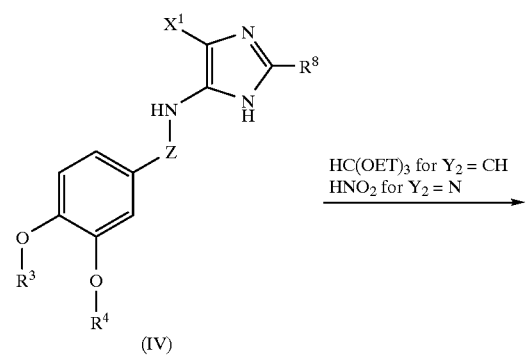

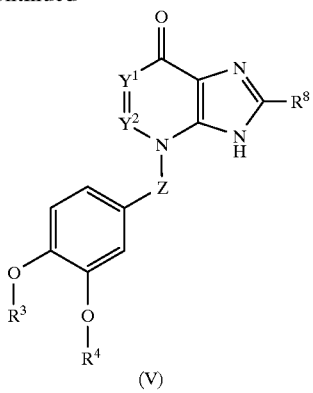

(V)

wherein $X_1$ is a carboxamide, Z is $CH_2$ and $Y_1$ is N. To yield compound (V) wherein $Y_2$ is CH, the cyclization occurs using a suitable ester, particularly preferred is triethylorthoformate. To yield compound (V) wherein $Y_2$ is N, the cyclization occurs using nitrous acid.

Step (c) of the synthetic scheme involves the 6-oxo group of compound (V) being transformed to the amine by successive halogenation (e.g. chlorination) and displacement to give compound (I), for example as shown below:

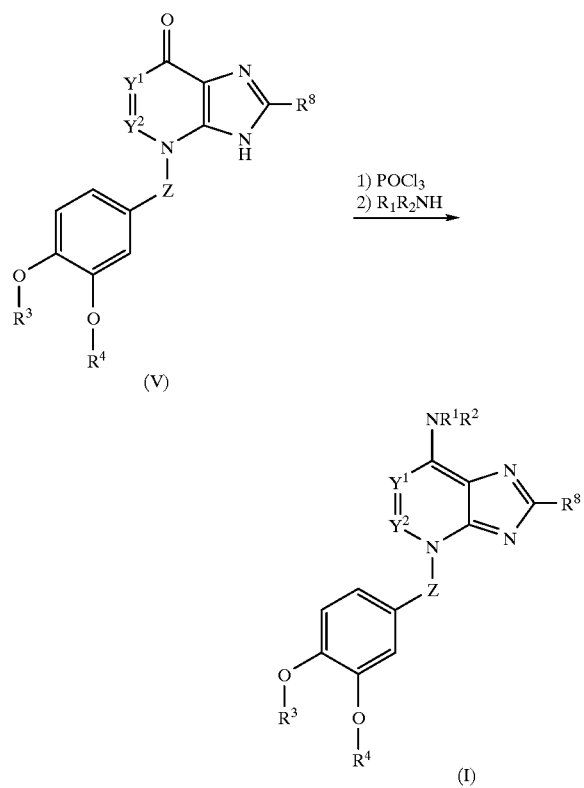

wherein Z is $CH_2$ and $Y_1$ is N.

The halogenation agent is preferably a chlorinating agent, e.g. phosphorous oxychloride, thionyl chloride or oxalyl chloride. The halogenation step may occur in a suitable solvent, e.g. DMF. The halogenated intermediate is then reacted with an amine to form compound (V) in an alcoholic or aqueous solution. The halogenation and displacement reactions can occur at any suitable temperature range, preferably less than about 50° C.

The synthetic pathway described in Scheme 2 is a modification of Scheme 1. Scheme 2 can be used to obtain compounds of formula 1 wherein Z is and $Y_1$ and $Y_2$ are CH. In Scheme 2, the imidazole starting material is substituted with an ester, rather than a carboxamide. The method for producing xanthine compounds of Scheme 2 is described as follows:

In step (a) of the synthetic scheme, compound (II) is subjected to reductive amination using a 2-step procedure employing the benzaldehyde of compound (III) in the presence of an acid, followed by reduction with a reducing agent to yield compound (IV) as shown below:

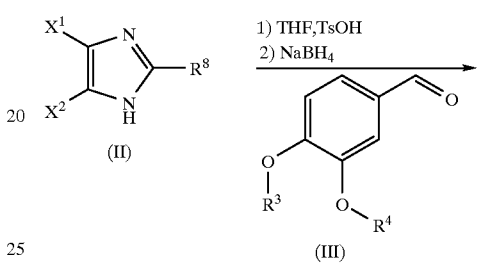

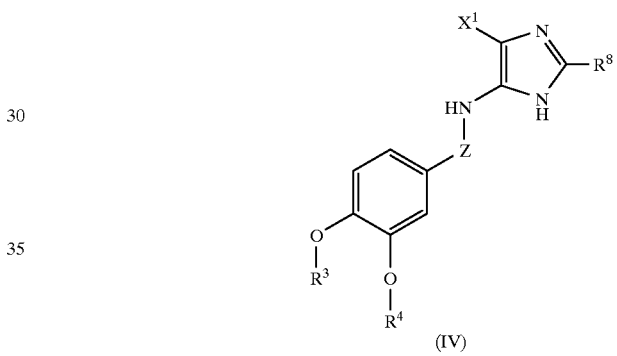

wherein $X^1$ is an ester, e.g. ethyl ester, $X^2$ is an amino group and Z is $CH_2$. The acid of this step can be any suitable acid, e.g. tosic acid or p-toluenesulfonic acid. Any suitable reducing agent can be used in this step, e.g. a borane anion such as sodium borohydride. The reaction of step (a) can occur in a suitable solvent e.g. methanol or THF.

Step (b) of the reaction involves cyclization of compound (IV) to form the hypoxanthine of compound (V):

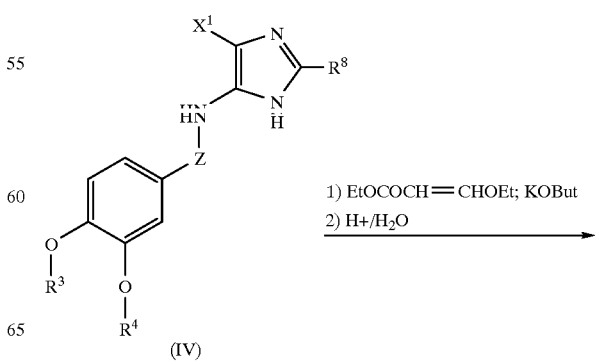

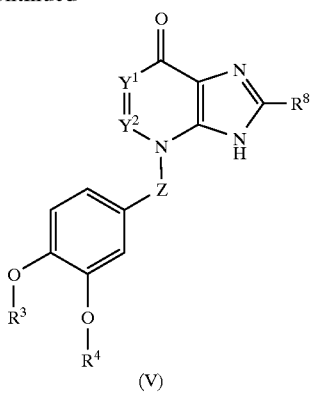

Wherein $X_1$ is an ester e.g. ethyl ester, Z is $CH_2$ and $Y_1$ and $Y_2$ are CH. The cyclization can occur using a propenoate, e.g. ethyl 3-ethoxyacrylate, with a base, e.g. a sodium alkoxide or potassium alkoxide, such as potassium t-butoxide.

Step (c) of the synthetic scheme involves the 6-oxo group of compound (V) being transformed to the amine by successive halogenation (e.g. chlorination) and displacement to give compound (1) of the invention, for example as shown below:

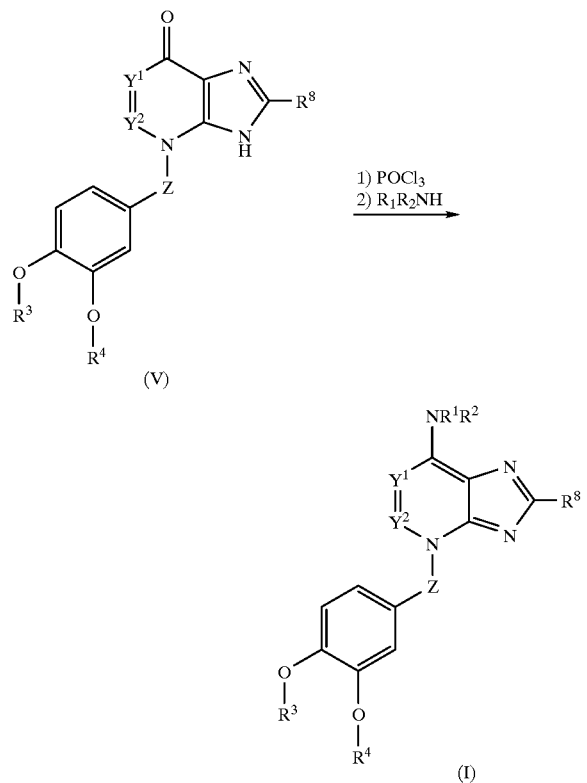

wherein Z is C and $Y_1$ and $Y_2$ are CH.

The halogenation agent is preferably a chlorinating agent, e.g. phosphorous oxychloride, thionyl chloride or oxalyl chloride. The halogenation step may occur in a suitable solvent, e.g. DMF. The halogenated intermediate is then reacted with an amine to form compound (V) in an alcoholic or aqueous solution. The halogenation and displacement reactions can occur at any suitable temperature range, preferably less than about 50° C.

The synthetic pathway described in Scheme 3 is a modification of Scheme 2. Scheme 3 can be used to obtain compounds of formula 1 wherein $Y_1$ and $Y_2$ are CH. In Scheme 3, the imidazole starting material is di-substituted with halogen. The method for producing xanthine compounds of Scheme 3 is described as follows:

In step (a) of the synthetic scheme, compound (II), substituted at the $X_1$ and $X_2$ positions with halogen, preferably bromine, is the starting material. One of the halogens is replaced with cyanine, e.g. by reaction with cuprous cyanine, and the resultant nitrile is hydrolyzed to a carboxylic acid, and then transformed into an ester. After the formation of the ester, the other bromine is replaced with the amine by reaction with formula (X) to yield compound (IV) as shown below:

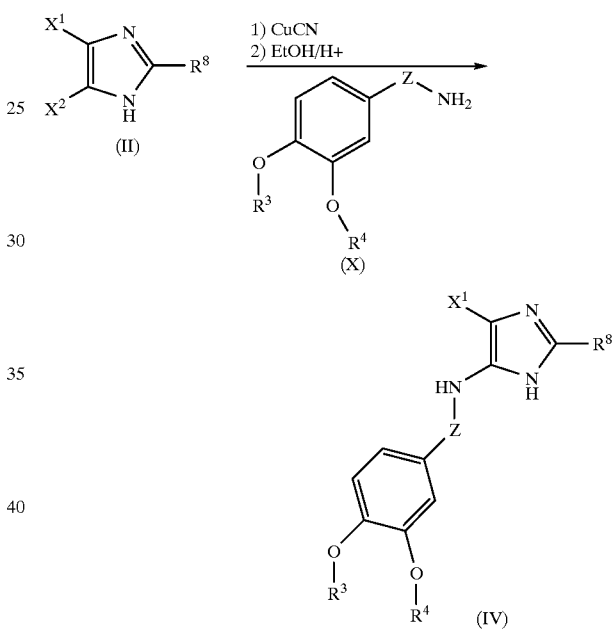

wherein $X_1$ is a halide, e.g. bromide.

Step (b) of the reaction involves cyclization of compound (IV) to form the hypoxanthine of compound (V):

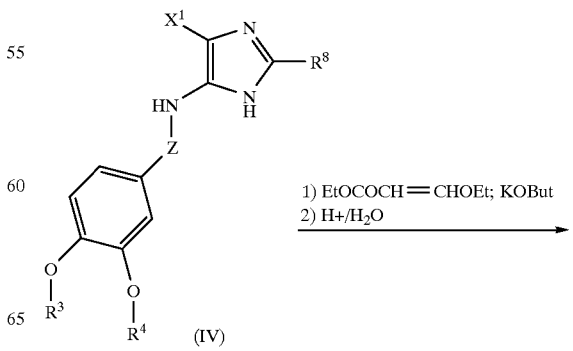

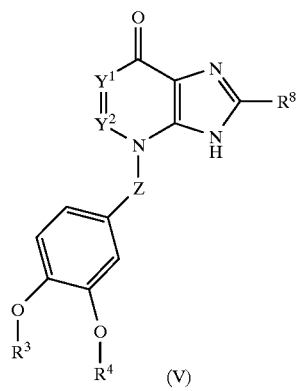

(V)

wherein $Y_1$ and $Y_2$ are CH.

The cyclization can occur using a propenoate, e.g. ethyl 3-ethoxyacrylate, with a base, e.g. a sodium alkoxide or potassium alkoxide, such as potassium t-butoxide.

Step (c) of the synthetic scheme involves the 6-oxo group of compound (V) being transformed to the amine by successive halogenation (e.g. chlorination) and displacement to give compound (I) of the invention, for example as shown below:

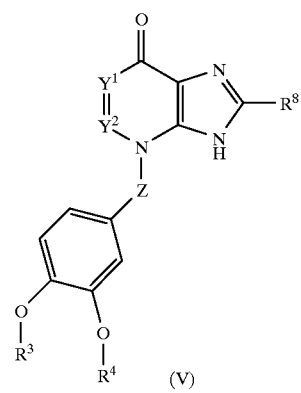

(V)

1) POCl$_3$
2) R$_1$R$_2$NH

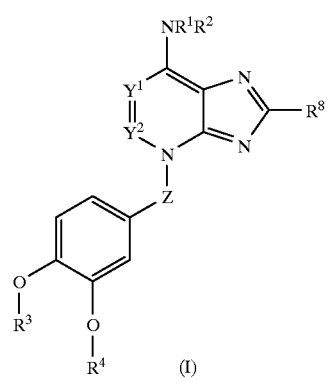

(I)

wherein $Y_1$ and $Y_2$ are CH.

The halogenation agent is preferably a chlorinating agent, e.g. phosphorous oxychloride, thionyl chloride or oxalyl chloride. The halogenation step may occur in a suitable solvent, e.g. DMF. The halogenated intermediate is then reacted with an amine to form compound (V) in an alcoholic or aqueous solution. The halogenation and displacement reactions can occur at any suitable temperature range, preferably less than about 50° C.

The synthetic pathway described in Scheme 4 uses similar chemistry as shown in Schemes 1 and 3. Scheme 4 is used to obtain compounds of formula I wherein $Y_1$ is N. In Scheme 3, the imidazole starting material is di-substituted with halogen. The method for producing xanthine compounds of Scheme 3 is described as follows:

In step (a) of the synthetic scheme, compound (II), substituted at the $X_1$ and $X_2$ positions with halogen, preferably bromine, is the starting material. One of the bromines is replaced with cyanine, e.g. by reaction with cuprous cyanine, and the resultant nitrile is reacted to form a carboxamide. After the formation of the carboxamide, the other bromine is replaced with the amine by reaction with formula (X) to yield compound (IV) as shown below:

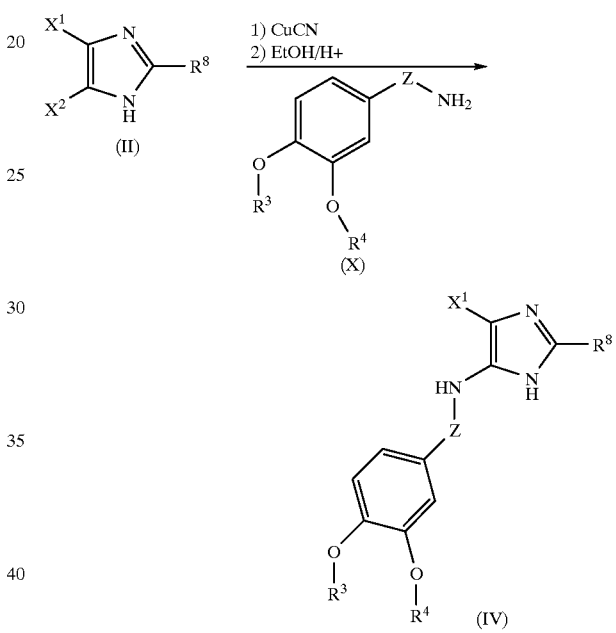

wherein $X_1$ is a carboxamide.

Step (b) of the reaction involves cyclization of compound (IV) to form the hypoxanthine of compound (V):

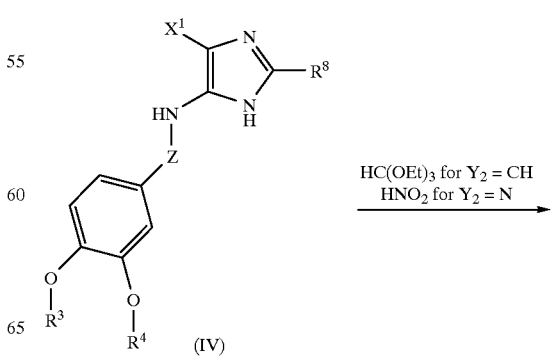

HC(OEt)$_3$ for $Y_2$ = CH
HNO$_2$ for $Y_2$ = N

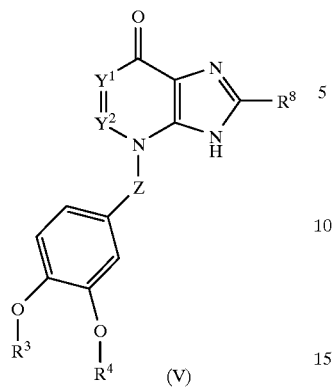

wherein $Y_1$ is N.

To yield compound (V) wherein $Y_2$ is CH, the cyclization occurs using a suitable ester, particularly preferred is triethylorthoformate. To yield compound (V) wherein $Y_2$ is N, the cyclization occurs using nitrous acid.

Step (c) of the synthetic scheme involves the 6-oxo group of compound (V) being transformed to the amine by successive halogenation (e.g. chlorination) and displacement to give compound (1) of the invention, for example as shown below:

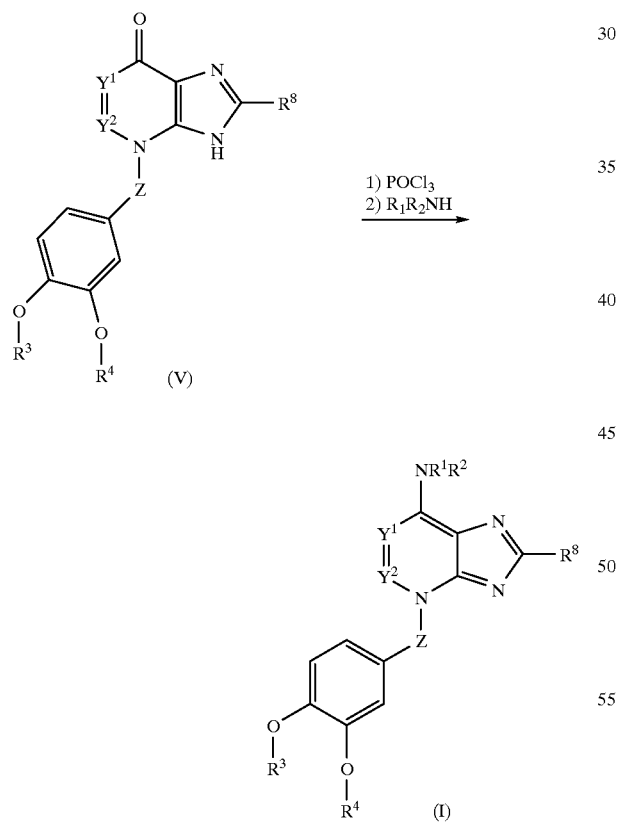

wherein $Y_1$ is N.

The halogenation agent is preferably a chlorinating agent, e.g. phosphorous oxychloride, thionyl chloride or oxalyl chloride. The halogenation step may occur in a suitable solvent, e.g. DMF. The halogenated intermediate is then reacted with an amine to form compound (V) in an alcoholic or aqueous solution. The halogenation and displacement reactions can occur at any suitable temperature range, preferably less than about 50° C.

EXAMPLE 1

3-(3-Cyclopentyloxy-4-methoxybenzyl)-6-ethylamino-8H-purine

The title compound was prepared by the following synthetic pathway:

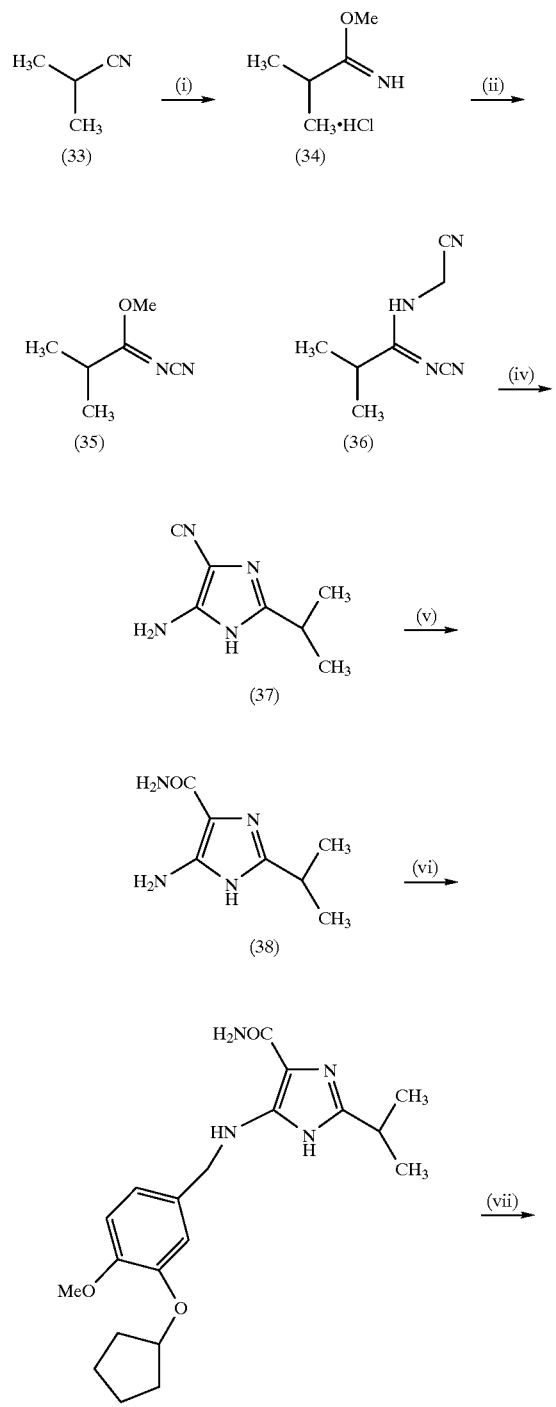

-continued

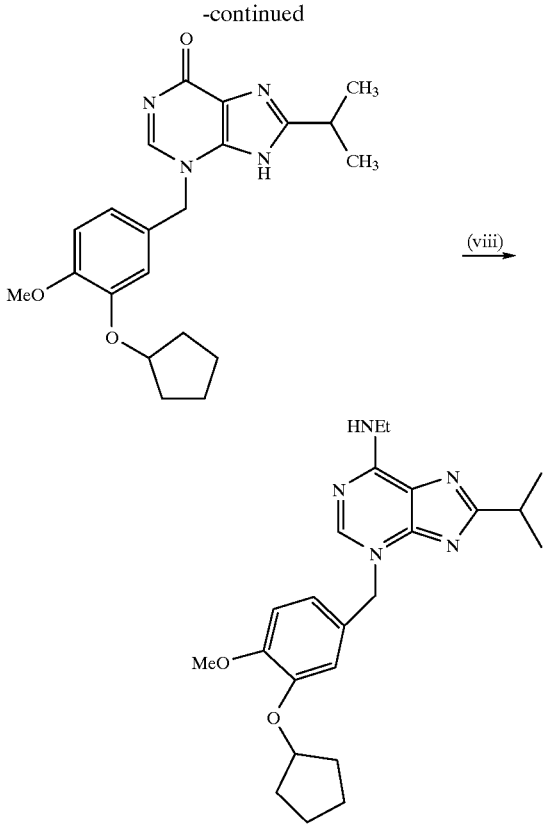

The pathway occured under the conditions as set forth below. The pathway can occur under other suitable conditions known in the art and the particular conditions disclosed herein are not meant to be limiting.

(i) Preparation of Methyl 2-Methylpropionimidate Hydrochloride (a) A water bath was placed on a 16-kg balance. A 4-L Erlenmeyer flask was placed in the water bath and fitted with a thermometer and a gas inlet tube. A mechanical stirring apparatus was suspended over the flask with sufficient agitator clearance to enable the addition of materials to the flask Methyl-tert-butyl ether (3.0 L) was added to the flask and ice water was added to the water bath. The stirrer was started and set for moderate agitation.

(b) The balance was tared. To the methyl tert-butyl ether was charged, through the gas inlet tube, anhydrous hydrogen chloride gas (420 g) over one hour. The rate of addition was controlled to maintain the batch temperature below 20° C.

(c) After the addition of anhydrous hydrogen chloride gas was complete, the solution was cooled to 5° C.

(d) Methanol (387.4 g) and isobutyronitrile (717.0 g) were combined and mixed for five minutes to obtain a uniform solution.

(e) The solution prepared in (d) was added dropwise to the batch, at a rate to maintain the batch temperature below 10° C. The resulting clear solution was allowed to warm to room temperature (23° C.) with continued stirring overnight. During the overnight stir, the product crystallized from the solution.

(f) The thick, white suspension was cooled in an ice/water bath to below 5° C. and stirred for approximately two hours.

(g) A 4-L filtration flask attached to a Gast® vane vacuum pump was assembled with a 253-mm Büchner funnel containing Sharkskin™ filter paper. The vacuum pump was started, the filter paper was wetted with methyl tert-butyl ether (100 mL) and pressed in place. After confirming a complete seal of the filter paper, the suspension from Step (f) was vacuum filtered and washed with methyl tert-butyl ether (500 mL).

(h) The first crop of product, methyl 2-methylpropionimidate hydrochloride, was air dried, weighed, transferred to a polyethylene bag, and stored at room temperature.

(i) The filtration from Step (g) was stored, without stirring, in a freezer (−10° C.) for three days. During the storage, the product crystallized from the solution.

(j) A 4-L filtration flask attached to a Gast® vane vacuum pump was assembled with a 150-mm Büchner funnel containing Sharkskin™ filter paper. The vacuum pump was started, the filter paper was wetted with methyl tert-butyl ether (100 mL) and pressed in place. After confirming a complete seal of the filter paper, the suspension from (i) was vacuum filtered and washed with methyl tert-butyl ether (200 mL).

(k) The second crop of product, methyl 2-methylpropionimidate hydrochloride, was air dried, weighed, transferred to a polyethylene bag, and stored at room temperature.

(l) The filter from (j) was stored, without stirring, in a freezer (−10° C.) for two weeks. During the storage, the product crystallized from the solution.

(m) A 4-L filtration flask attached to a Gast® vane vacuum pump was assembled with a 150-mm Büchner funnel containing Sharkskin™ filter paper. the vacuum pump was started, the filter paper was wetted with methyl tert-butyl ether (100 mL) and pressed in place. After confirming a complete seal of the filter paper, the suspension from (l) was vacuum filtered and washed with methyl tert-butyl ether (200 mL).

(n) The third crop of product, methyl 2-methylpropionimidate hydrochloride, was air dried, weighed, transferred to a polyethylene bag, and stored at room temperature.

(ii) Preparation of 2-Methylpropion-N-cyanoimidate (a) To a 25-L, polypropylene pall equipped with an overhead, mechanical stirrer and thermometer was charged methyl 2-methylpropionimidate hydrochloride (1507.0 g) and cold (approximately 2° C.) cyanamide, 50% aqueous solution (111.8 g).

(b) The stirrer was started and set a high speed to obtain a vigorous agitation. Sodium -hydrogen phosphate dodecahydrate (5910.0 g) was added, in 200–300 g portions, over 2.25 hours. The pH of the reaction mixture was monitored with pH paper. The pH range was maintained between 5–6 during the sodium hydrogen phosphate dodecahydrate addition by the addition of water (4×300.0 mL), in portions.

(c) After the addition was completed, the slurry was stirred for one hour. The slurry thickened. Water (500 mL) and methyl tert-butyl ether (1.0 L) were added and the slurry was stirred for an additional two hours.

(d) A filtration apparatus attached to a Gast® vane vacuum pump was assembled with an 18.6-cm Büchner funnel containing Sharkskin™ filter paper. The filter paper was wetted with methyl tert-butyl ether (100.0 mL) and pressed in place. After confirming a complete seal of the filter paper, the solution from (c) was vacuum filtered and the filter cake was washed with methyl tert-butyl ether (2×500.0 mL).

(e) The filtrate was transferred to a 5-L separatory funnel and allowed to separate for approximately ten minutes. The layers were separated. The lower (aqueous) layer was transferred to a second 5-L separatory fiu0el. The upper (organic) layer was drained into an appropriate container and set aside for later use.

(f) The aqueous layer, from (e) was washed with methyl tert-butyl ether (500.0 mL) and the biphasic mixture was allowed to separate for approximately ten minutes. The lower (aqueous) layer was drained into the appropriate container and discarded.

(g) The organic phase from (f) was combined the organic phase from (e)

(h) Sodium sulfate (100.0 g) was added to the combined organic phases. This mixture was gently stirred, with a glass stirring rod, intermittently, for approximately 30 minutes.

(i) A filtration apparatus attached to a Gast® vane vacuum pump was assembled with a filter funnel containing Sharkskin™ filter paper. The filter paper was wetted with methyl tert-butyl ether (100.0 mL) and pressed in place. After confirming a complete seal of the filter paper, the solution from (h) was vacuum filtered and the filter cake was washed with methyl tert-butyl ether (250.0 mL).

(j) The combined filtrate and the washings were transferred in portions to a 3-L rotary evaporator bulb that was connected to a rotary evaporator. The entire solution containing the product was concentrated under vacuum (approximately 23 to 26 inches Hg vacuum) to a constant weight. The product, methyl-methylpropion-N-cyanoimidate, was used directly in the next step.

(iii) Preparation of 2-Methylpropion-N-cyanomethylamidine (a) A four-neck, 5-L, round bottom flask was equipped with an overhead mechanical stirrer, a gas dispersion tube, a 500-mL addition funnel with a pressure equalizing arm, and a thermometer. The apparatus was placed in an empty water bath and charged with methanol (300 mL). The stirrer was started and nitrogen gas was bubbled through the solution for 30 minutes.

(b) The reactor was charged with methyl 2-methylpropion-N-cyanoimidate (264.6 g) and aminoacetonitrile hydrochloride (317.8 g). The reaction mixture was stirred and the bubbling of nitrogen was continued for 15 minutes.

(c) Triethylamine (408.4 g) was charged to the dropping funnel. The empty water bath was filled with ice/water and the reaction mixture was cooled to below 20° C.

(d) The triethylamine (408.4 g) was added at a rate to maintain the batch temperature below 40° C. The mixture was stirred at room temperature for approximately 12 hours after the addition was complete. The reaction completion was checked by TLC analysis.

(e) A 4-L polypropylene beaker was placed into an empty water bath, fitted with a mechanical stirrer and charged with water (2.0 L). The stirrer was started and set a high speed to obtain a vigorous agitation. The contents of the flask from (d) were poured into the water, with continued stirring.

(f) An ice/water mixture was added to the water bath and cooling with vigorous stirring was maintained for approximately 1.5 hours. During this time, the product crystallized as a cream-colored solid.

(g) A filtration apparatus attached to a Gast® vane vacuum pump was assembled with an 18.6-cm Büchner funnel containing Sharkskin™ filter paper. The filter was wetted with water (100 mL) and pressed in place. After confirming a complete seal of the filter paper, the solution from (f) was filtered and the filter cake was washed with ice cold water (300 mL).

(h) The filter cake was air dried on the filter for approximately two hours (until the dripping of the filtrate into the receiver was negligible.).

(i) The solid was placed onto tared, glass drying pans and transferred to a drying oven. The solid was vacuum dried to constant weight using a high-vacuum pump (29 inches Hg vacuum) at 55° C. for approximately 72 hours.

(j) The dried compound, 2-methylpropion-N-cyano-N'-cyanomethylamidine, was removed from the oven, weighed, and transferred to an amber glass bottle for storage at ambient temperature.

(iv) Preparation of 4-Amino-5cyano-2-(2-methylethyl) imidazole (a) A 5-L, three-neck, round-bottom flask was fitted with a mechanical stirrer, nitrogen inlet, and a thermometer. Methyl 2-methylpropio-N-cyano-N'-cyanomethylamidine (450 g) and tetrahydrofuran (2.0 L) were charged to the flask and the stirrer was started. The mixture was stirred for 30 minutes at ambient temperature.

(b) To this heterogenous mixture, potassium tert-butoxide (673 g) was added in portions over two hours. The temperature was maintained between 30° C. and 40° C. by controlling the addition rate. At a temperature of 30° C., a homogeneous solution was obtained.

(c) After the addition of potassium tert-butoxide, the pale brown solution was stirred for an additional ten minutes at 40° C. The reaction completion was monitored by thin layer chromatography (TLC).

(d) To this reaction mixture, methanol (500 mL) was added and the solution was cooled to 5° C. using an ice bath.

(e) Concentrated hydrochloric acid (600 g of a 36% solution) was added over one hour at such a rate to maintain the batch temperature below 20° C. using an ice/water bath.

(f) A 4-L filtration apparatus attached to a Gast® vane vacuum pump was assembled with a 27-cm Büchner funnel containing filter paper. The filter paper was wetted with methanol (10 mL) and pressed in place. After confirming a complete seal of the filter paper, the solution from (e) was filtered and collected.

(g) The precipitate was then washed with methanol (2×500 mL) and the washings were collected.

(h) The filtrates from (f) and (g) were combined and transferred to a 3-L evaporator bulb that was connected to a rotary evaporator. The content of the bulb was concentrated to =minimum volume under reduced pressure (approximately 25 inches Hg vacuum).

(i) Toluene (2.250 mL) was added to the 3-L evaporator bulb, and the contents of the bulb were further concentrated.

(j) To the 3-L evaporator bulb containing the clear, brown solution, ethyl acetate (1500 mL) was added and the solution was heated at reflux for one hour.

(k) A 4-L filtration apparatus attached to Gast® vane vacuum pump was assembled with a 10-cm Büchner funnel containing filter paper. The filter paper was wetted with ethyl acetate (10 mL) and pressed in place. After confirming a complete seal of the filter paper, the hot ethyl acetate mixture from (j) was clarified and the filtrate was collected.

(l) The filtrate was stored in the refrigerator (5° C.) overnight, and the product precipitated.

(m) A 2-L filtration apparatus attached to a Gast® vane vacuum pump was assembled with a 24-cm Büchner funnel containing filter paper. The filter paper was wetted with ethyl acetate (10 mL) and pressed in place. After confirming a complete seal of the filter paper, the suspension from (l) was filtered.

(n) The product, 4-amino-5-cyano-2-(2-methylethyl) imidazole, was washed with cold (5° C.) ethyl acetate (250 mL) and air-dried.

(o) The filtrate from (m) was transferred to a 3-L evaporator bulb that was connected to a rotary evaporator. The contents of the evaporator bulb were concentrated to approximately 500 mL under reduced pressure (27 inches Hg vacuum).

(p) The rotary evaporator bulb and its contents were placed in an ice bath for five hours, and additional product crystallized.

(q) A 1-L filtration apparatus attached to a Gast® vane vacuum pump was assembled with a 10-cm Büchner funnel containing filter paper. The filter paper was wetted with ethyl acetate (10 mL) and pressed in place. After confirming a compete seal of the filtered paper, the solution from (p) was filtered.

(r) The product, 4-amino-5-cyano-2-(2-methylethyl) imidazole, was washed with cold ethyl acetate (100 mL).

(s) The wet first and second crops (from (n) and (r), respectively) were combined and dried at 60° C. overnight in a vacuum drying oven.

(v) Preparation of 4-Amino-2-(2-methylethyl)imidazole-5-carboxamide (a) A three-neck, 2-L, round bottom flask was placed in an electric heating mantle, fitted with an overhead mechanical stirrer, additional funnel, and a thermometer. Sulfuric acid, 96.3% (152.6 g) was charged to the flask and the stirrer was started.

(b) Water (10.8 g) was added to the dropping funnel. The water was added dropwise to the stirring acid. The mixture was stirred approximately five minutes after the addition was complete to ensure homogeneity.

(c) 4-Amino-5-cyano-2-(2-methylethyl)imidazole (131.6 g) was added in portions until the temperature reached approximately 90° C. A slower addition was continued at such a rate to maintain the batch temperature above 90° C. but not to exceed 100° C. The addition time was approximately two hours. After the addition was complete, the temperature was maintained between 90° C. and 100° C. by gentle heating for 30 minutes. The batch was then assayed for completeness of reaction by TLC.

(d) The three-neck, 2-L, round-bottom flask containing the thick reaction mixture was removed from the heating mantle and placed in a water bath. The bath was filled with an ice water mixture and the stirred reaction mixture was cooled to approximately 40° C.

(e) To this reaction mixture, methanol (250 mL) was cautiously added with efficient stirring at such a rate to maintain the batch temperature below 40° C. with ice bath cooling.

(f) Upon complete addition, the reaction mixture was stirred with ice bath cooling below 20° C. The stirrer was set to stir rapidly and sodium bicarbonate (450.0 g) was added in portions over three hours.

(g) To the thick slurry was added water (250.0 mL) and the mixture was stirred for one hour until a granular precipitate formed.

(h) A 20-cm Büchner funnel was assembled with a 2-L filtration flask receiver and the apparatus was attached to a Gast® vane vacuum pump. Filter paper was placed in the funnel and the vacuum pump was turned on. The filter paper was wetted with methanol (20 mL) and pressed in place. After confirming a complete seal of the filter paper, the suspension was vacuum filtered.

(i) The filter cake was washed with methanol (250 mL). The filter cake was manually compacted to minimize cracking and suction was maintained until very little filtrate was observed dripping into the receiver.

(j) The filter was transferred to a 3-L, round-bottom flask, placed on a rotary evaporator, and concentrated to a volume of approximately 500 mL.

(k) The flask was removed from the evaporator and placed in an ice water cooling bath. The flask was fitted with an overhead mechanical stirrer and the contents were stirred with cooling to 5° C. for about four hours.

(l) A 14-cm Büchner funnel was assembled with a 2-L filtration flask receiver and the apparatus was attached to a Gast® vane vacuum pump. Filter paper was placed in the funnel and the vacuum pump was turned on. The filter paper was wetted with methanol (20 mL) and pressed in place. After confirming a complete seal of the filter paper, the suspension was vacuum filtered.

(m) The filter cake was placed in a tared, glass drying pan and dried at 60° C. in a vacuum oven (30 inches Hg vacuum) for approximately 15 hours.

(n) The dried product, 4-amino-2-(2-methylethyl) imidazole-5-carboxamide, was removed from the oven, weighed, transferred to a polyethylene bag, and stored at ambient temperature.

(o) The filtrate from (1) was transferred to a 1-L, round bottom flask, placed on a rotary evaporator, and concentrated to a volume of approximately 100 mL.

(p) A 10-cm Büchner funnel was assembled with a 2-L filtration flask receiver and the apparatus was attached to a Gast® vane vacuum pump. Filter paper was placed in the funnel and the vacuum pump was turned on. The filter paper was wetted with methanol (20 mL) and pressed in place. After confirming a complete seal of the filter paper, the suspension was vacuum filtered.

(q) The filter cake was placed in a tared, glass drying pan and dried at 60° C. in a vacuum oven (30 inches Hg vacuum) overnight for 14 hours.

(r) The dried product, 4-amino-2-(2-methylethyl) imidazole-5-carboxamide, was removed from the oven, weighed, transferred to a polyethylene bag, and stored at ambient temperature.

(s) The dried products from (n) (First Crop) and (r) (Second Crop) were combined, weighed, transferred to a polyethylene bag, and stored at ambient temperature.

(vi) Preparation of 4-(3-cyclopentyloxy-4-methoxybenzylamino)-2-(2-methylethyl)imidazole-5-carboxamide (a) A three-neck, 250-mL, round-bottom flask was placed in an electric heating mantle and equipped with a mechanical stirrer and a thermometer. Methanol (60 mL) was added and stirring was initiated. 4-Amino-2-(2-methylethyl) imidazole-5-carboxamide (12.6 g), p-toluenesulfonic acid, monohydrate (0.14 g), and 3-cyclopentyloxy-4-methoxybenzaldehyde (17.6 g) in methanol (15 mL) were added sequentially and the suspension was stirred.

(b) The reaction mixture was stirred for one hour. The batch was then analyzed by TLC to monitor the consumption of 4-amino-2-(2-methylethyl)imidazole-5-carboxamide (starting material).

(c) The reaction flask was fitted with a distillation head and a water-cooled distillation condenser and receiving flask. The heating mantle was plugged into a Variac power transformer. The power transformer was set to approximately 30% power and turned on. The reaction was heated to the boiling point.

(d) Upon reaching the boiling point, the solvent began to distill out. Approximately 30 mL of solvent was removed by atmospheric distillation. The heating was stopped and the heating mantle was replaced with an empty water bath.

(e) A mixture of ice/water was added to the water bath. The mixture was cooled with stirring until the temperature dropped below 20° C. and the ice bath was removed.

(f) Toluene (30 mL) was added to the mixture. The flask was fitted with a powder additional funnel and sodium borohydride (5.96 g) was added as a suspsension in ethanol (40 mL) over approximately ten minutes with stirring.

(g) The heating mantle was plugged into a Variac power transformer. The power transformer was set to approximately 30% power and turned on. The reaction mixture was heated to approximately 40° C.

(h) The reaction mixture was heated at approximately 40° C. for one hour. The progress of imine reduction was monitored by TLC.

(i) When the reaction was determined to be complete, the heating was stopped and the stirring mixture was allowed to cool to room temperature.

(j) The reaction mixture was poured into water (60 mL) and the aqueous solution was extracted with ethyl acetate (3×70 mL).

(k) The organic extracts were combined and treated with magnesium sulfate (10 g). The aqueous solution was discarded.

(l) A 5.3-cm Büchner funnel was assembled with a 500-mL filtration flask receiver and the apparatus was attached to a Gast® vane vacuum pump. Filter paper was placed in the funnel and the vacuum pump was turned on. The filter paper was wetted with ethyl acetate (5 mL) and pressed in place. After confirming a complete seal of the filter paper, the suspension was vacuum filtered. The drying agent was washed with ethyl acetate (approximately 20 mL).

(m) The solution was transferred to a 500 mL, one-neck, round-bottom flask, which was connected to a rotary evaporator. The solution was concentrated to a volume of approximately 60 mL.

(n) The flask was removed from the rotary evaporator and placed in an empty water bath on a magnetic stirring plate. Ethyl acetate (30 mL) was added and the stirrer was started. Ice/water was added to the bath and the mixture was stirred with cooling for four hours.

(o) A 5.3-cm Büchner funnel was assembled with a 250-mL filtration flask receiver and the apparatus was attached to a Gast® vane vacuum pump. Filter paper was placed in the funnel and the vacuum pump was turned on. The filter paper was wetted with ethyl acetate (approximately 5 mL) and pressed in place. After confirming a complete seal of the filter paper, the suspension was vacuum filtered. The solid was washed with ethyl acetate (approximately 10 mL). The filter cake was manually compacted to minimize cracking and suction was maintained until very little filtrate was observed dripping into the receiver.

(p) The filter cake was placed in a tared, glass drying pan and dried at 60° C. in a vacuum oven (2 mm Hg vacuum) for approximately 15 hours.

(q) The dried product 4-(3-cyclopentyloxy-4-methoxybenzylamino)-2-(2-methylethyl)imidazole-5-carboxamide, was removed from the oven, weighed, transferred to an amber glass bottle, and stored at ambient temperature.

(vii) Preparation of 3-(3-cyclopentyloxy-4-methoxybenzyl)-8-(2-methylethyl) hypoxanthine (a) A three-neck, 250-mL, round-bottom flask was placed in an electric heating mantle, on a magnetic stirring plate and fitted with a distillation head with a water cooled distillation condenser and a thermometer. A magnetic stirring bar was placed in the flask. 4-(3-Cyclopentyloxy-4-methoxybenzylamino)-2-(2methoxybenzylamino)-2-(2-methylethyl)imidazole-5-carboxamide (17.5 g), triethylorthoformate (12 mL), p-toluenesulfonic acid, monohydrate (approximately 50 mg), and toluene (50 mL) were charged to the flask and the stirrer was started.

(b) The heating mantle was plugged into a Variac power transformer. The power transformer was set to approximately 30% power and turned on).

(c) The heating continued and the temperature was allowed to increase until noticeable reflux of the mixture was attained.

(d) Reflux was maintained and the distillate was collected. During this period the internal temperature of the mixture rose to 110° C. The batch was then analyzed by TLC.

(e) The three-neck, 250 mL, round-bottom flask containing the reaction mixture was removed from the heating mantle and placed in a water bath. The bath was filled with an ice/water mixture and the reaction was cooled with stirring to approximately 5° C.

(f) The reaction mixture was stirred with continued cooling for approximately one hour.

(g) A 8.3-cm Büchner funnel was assembled with a 250-mL filtration flask receiver and the apparatus was attached to a Gast® vane vacuum pump. Filter paper was placed in the funnel and the vacuum pump was turned on. The filter paper was wetted with toluene (10 mL) and pressed in place. After confirming a complete seal of the filter paper, the suspension was vacuum filtered.

(h) The filter cake was washed with toluene (25 mL). The filter cake was manually compacted to minimize cracking and suction was maintained until very little filtrate was observed dripping into the receiver.

(i) The filter cake was placed in a tared, glass drying pan and dried at 60° C. in a vacuum oven (2 mm Hg vacuum) for approximately 15 hours.

(j) The dried product, 3-(cyclopentyloxy-4-methoxybenzyl)-8-(2-methylethyl) hypoxanthine, was removed from the oven, weighed, transferred to an amber glass bottle, and stored at ambient temperature.

(k) The filtrate from Step (h) was transferred to a 250-mL, single-neck round-bottom flask, placed on a rotary evaporator, and concentrated to a volume of approximately 20 mL.

(l) The flask was removed from the evaporator, treated with ethyl acetate (30 mL) and placed in an ice/water cooling bath. The contents were magnetically stirred, with cooling to below 5° C. for about two hours.

(m) A 4.3-cm Büchner funnel was assembled with a 125-mL filtration flask receiver and the apparatus was attached to a Gast® vane vacuum pump. Filter paper was placed in the funnel and the vacuum pump was turned on. The filter paper was wetted with ethyl acetate (2 mL) and pressed in place. After confirming a complete seal of the filter paper, the suspension was vacuum filtered.

(n) The filter cake was washed with ethyl acetate (10 mL). The filter cake was manually compacted to minimize cracking and suction was maintained until very little filtrate was observed dripping into the receiver.

(o) The filter cake was placed in a tared, glass drying pan and dried at 60° C. in a vacuum oven (2 mm Hg vacuum) for approximately 15 hours.

(p) The dried product, 3-(cyclopentyloxy-4-methoxybenzyl)-8-(2-methylethyl)-hypoxanthine, was removed from the oven, weighed, transferred to an amber glass bottle, and stored at ambient temperature.

(viii) Preparation of 3-(3-cyclopentyloxy-4-methoxybenzyl)-6-ethylamino-8-isopropyl-3H-purine (1) A 12-L, three-neck, round-bottom reactor in an empty plastic cooling bath was fitted with an overhead stirrer, six-inch powder funnel, 500-mL pressure equalizing addition funnel, thermometer, and nitrogen bubbler. Methylene chloride (5.0 L) and N,N-dimethylfoemamide (390 mL)

were added through the powder funnel. The nitrogen gas flow was started.

(2) The plastic cooling bath was filled with an ice/water mixture. The stirrer was started and the reaction mixture was cooled to 5° C. to 10° C.

(3) Phosphorous oxychloride (475 mL) was added to the addition funnel, then added to the reaction mixture at a rate (about 15 mL/minute) to maintain the batch temperature below 15° C. After the addition was complete, the mixture was stirred for 30 minutes.

(4) The hypoxanthine was added, in portions, to maintain the reaction temperature below 15° C. The weight vessel was rinsed with methylene chloride (355 mL) and the rinse was added to the reaction mixture.

(5) The reaction mixture was allowed to warn to room temperature (16° C.) and it was stirred for approximately 16 hours.

(6) The cooling bath was emptied and an ice/water mixture was added to the bath to lower the batch temperature below 10° C.

(7) Water (1.0 L) was added dropwise at a rate of approximately 21 mL/minute to the reaction solution (total addition time was 48 minutes).

(8) After the addition of the water was completed, the reaction mixture was stirred for about one-half hour with external cooling.

(9) Diisopropyl ether (4.0 L) was added to the reaction solution and the mixture was stirred for approximately ten minutes.

(10) The stirring of the reaction solution was stopped. The biphasic solution was charged to a 22-L separatory funnel. The reaction was rinsed with methylene chloride (415 mL) and the rinse was transferred to the 22-L separatory funnel.

(11) Water (2.0 L) was added and the biphasic solution was stirred with a high-speed stirrer for about 15 minutes, then the layers were allowed to separate. The lower (organic) layer was drained into an appropriate container. The upper (aqueous) layer was discarded.

(12) The lower (organic) layer was returned to the 22-L separatory funnel. Methylene chloride (415 mL) was used to rinse the container and the rinse was added to the separatory funnel. Water (2.0 L) was added and the mixture was stirred with a high-speed stirrer for about ten minutes, then the layers were allowed to separate. The lower (organic) layer was drained into an appropriate container. The upper (aqueous) layer was discarded.

(13) The lower (organic) layer was returned to the 22-L separatory funnel. Methylene chloride (420 mL) was used to rinse the container and the rinse was added to the separatory funnel. Water (2.0 L) was added and the mixture was stirred with a high-speed stirrer for about ten minutes, then the layers were allowed to separate. The lower (organic) layer was drained into an appropriate container. The upper (aqueous) layer was discarded.

(14) The lower (organic) layer was returned to the 22-L separatory funnel. The Methylene chloride (415 mL) was used to rinse the container and the rinse was added to the separatory funnel. Water (2.0 L) was added and the mixture was stirred with a high-speed stirrer for about ten minutes, then the layers were allowed to separate. The lower (organic) layer was drained into an appropriate container. The upper (aqueous) layer was discarded.

(15) The lower (organic) layer was returned to the 22-L separatory funnel. Methylene chloride (415 mL) was used to rinse the container and the rinse was added to the separatory funnel. Water (2.0 l) was added and the mixture was stirred with a high-speed stirrer for about ten minutes then the layers were allowed to separate. The lower (organic) layer was drained into an appropriate container. The upper (aqueous) layer was discarded.

(16) The lower (organic) layer was returned to the 22-L separatory funnel. Methylene chloride (420 mL) was used to rinse the container and the rinse was added to the separatory funnel. Diisopropyl ether (2×2.5 L) and water (3.0 L) were added and the mixture was stirred with a high-speed stirrer for 15 minutes. The layers were allowed to separate for a minimum of 30 minutes. The lower (organic) layer was drained into a 20-L Büchi rotary evaporator bulb. The upper (aqueous) layer was discarded.

(17) The batch was concentrated, at a bath temperature below 40° C., on a 20-L Büchi rotary evaporator using a Gast® van pump (26–28 inches Hg). Concentration was continued until no further condensate was visible in the condenser. The reaction mixture was checked by NMR for residual DMF content.

(18) Methylene chloride (2.0 L) was added to the batch and the mixture was rotated on the rotary evaporator without vacuum until it became homogeneous.

(19) A 12-L, three-neck, round-bottom reactor in an empty plastic cooling bath was fitted with an overhead stirrer and a six-inch powder addition funnel, and a 500 mL addition funnel. The stirrer was started and 70% ethylamine solution (2.0 L) was added through the powder funnel.

(20) The cooling bath was filled with an ice/water mixture and the solution from Step 19 was cooled to below 5° C.

(21) The reaction mixture from Step 18 was added to a pressure equalizing dropping funnel via a liquid funnel, then to the reactor at such a rate to maintain the temperature below 25° C. Methylene chloride (1.0 L) was used to rinse the reaction mixture container (from Step 18) and the rinse was added to the reactor.

(22) The reaction mixture was stirred for approximately one hour in an ice bath, then the mixture was then allowed to warm (17° C.) overnight (approximately 13 hours). After this point, the reaction was monitored by TLC for conversation to the title compound.

(23) After the reaction was determined to be complete, the reaction mixture was transferred to a 20-L Büchi rotary evaporator bulb. Methylene chloride (500 mL) was used to rinse the reactor (from Step 22) and the rinse was added to the rotary evaporator bulb.

(24) The reaction mixture was concentrated on the Büchi™ rotary evaporator using a Gast® van vacuum pump (25–27 inches Hg). concentration-was continued until no further condensate was visible.

(25) The thick oil from Step 24 was dissolved in methylene chloride (2.0 L).

(26) The reaction mixture was transferred to a 22-L separatory funnel. The rotary evaporator bulb was rinsed with methylene chloride (510 mL) and the rinse was added to the separatory funnel. Water (20 L) was then added and the contents of the separator funnel was stirred for approximately two minutes using a high-speed stirrer. The biphasic mixture was allowed to separate for approximately ten minutes.

(27) The lower, organic layer was separated into a suitable container and transferred to a 22-L separatory funnel. The upper (aqueous) layer was discarded. Methylene chloride (480 mL) was used to rinse the container and the rinse was added to the separatory funnel. Next, 1N sodium hydroxide solution (2.0 L) was added to the separatory funnel and the contents were stirred for approximately two minutes. The biphasic mixture was allowed to settle for approximately ten minutes.

(28) The lower, organic layer was separated into a suitable container and transferred to the 22-L separatory funnel. The upper (aqueous) layer was discarded. Methylene chloride (500 mL) was used to rinse the container and the rinse was added to the separatory funnel. Next, 1N aqueous sodium hydroxide solution (2.0 L) was added to the separatory funnel and the contents were stirred for approximately two minutes. The biphasic mixture was allowed to settle for approximately ten minutes.

(29) The lower, organic layer was separated into a suitable container and transferred to a 22-L separatory funnel. The upper (aqueous) layer was discarded. Methylene chloride (480 mL) was used to rinse the container and the rinse was added to the separatory funnel with two minutes of stirring between each addition. The biphasic mixture was allowed to settle for approximately ten minutes.

(30) The upper (aqueous) layer was discarded. The lower (organic) layer was separated into a container, decolorizing carbon (300 g) was added, and the mixture was stirred for approximately five minutes.

(31) A 12-L, three-neck, round-bottom reactor was fitted with a gast inlet/outlet adapter and the Büchner™ funnel (1860 mm) container filter paper was placed in one of the necks. The remaining unused neck was sealed with a glass stopper. The filtration apparatus was attached to a Gast® vane vacuum pump.

(32) The vacuum pump was turned on. The filter paper was wetted with methylene chloride (110 mL), pressed in place, and dry coated with celite (200 g). After confirming a complete seal of the filter paper, the reaction mixture from Step 30 was filtered. The reaction mixture container was rinsed with methylene chloride (510 mL) and the rinse was added to the funnel. Methylene chloride (1.0 L) was used to rinse the filter cake.

(33) The filtrate was transferred to a 20-L Büchi rotary evaporator and concentrated using a Gast® vane vacuum pump (25–27 inches Hg). Concentration was continued until no further condensate was visible in the container.

(34) A 22-L, three-neck, round-bottom reactor in a heating mantle was fitted with a water-cooled, vertical condenser, an overhead stirrer, and six-inch powder funnel.

(35) Acetonitrile (8.0 L) was added to the rotary evaporator bulb (from Step 33). The resulting solid suspension was stirred in the acetonitrile and then transferred to the 22-L reactor. Acetonitrile (2×4.0 L) was used to rinse the rotary evaporator bulb and the rinses were added to the 22-L reactor.

(36) The mixture was refluxed for approximately 15 minutes. The heat was then turned off and the mixture was allowed to cool (1° C.–2° C.) below reflux.

(37) Decolorizing carbon (306 g) was added and the mixture was refluxed for about ten minutes.

(38) A 22-L, three-neck, round-bottom reactor in a water bath was fitted with a gas inlet/outlet adapter and a Büncher funnel (186-mm) container filter paper was placed in one of the necks. The remaining unused neck was sealed with a glass stopper. The filtration apparatus was attached to a Gast® van vacuum pump.

(39) The vacuum pump was turned on. The filter paper was wetted with acetonitrile (110 mL), pressed in place, and dry coated with celite (223 g). After confirming a complete seal of the filter paper, the reaction mixture from Step 37 was filtered hot through the funnel. The reaction mixture container was washed with warm (approximately 50° C.) acetonitrile (2×500 mL) and the rinses were used to wash the filter cake.

(40) The reactor was an overhead stirrer. The stirrer was started and ice/water was added to the water bath. The filter was cooled to below 5° C. for a minimum of 15 minutes.

(41) A filtration apparatus consisting of a Büchner™ funnel (253-mm) with a rubber suction collar, was placed on the top of a 20-L carboy to receive the filtrate. The funnel was fitted with filter paper. The filtration apparatus was attached to a Gast® van vacuum pump.

(42) The vacuum pump was turned on. The filter paper was wetted with acetonitrile (110 mL), pressed in place. After confirming a complete seal of the filter paper, the contents of the 22-L reactor (from Step 5.40) were filtered. The filtered solids were washed with chilled (below 5° C.) acetonitrile (2×500 mL) followed by isopropyl acetate (2×500 mL). The filter cake was air dried until no further dripping from the tip of the funnel was observed.

(43) The solid was transferred from the filter to a 20-L Büchi rotary evaporator bulb. The solid was vacuum-dried on a rotary evaporator using a Gast® vane vacuum pump (greater than 25 inches Hg) at 50° C. for approximately 18 hours and then assayed by HPLC.

(44) A large glass column with a 3.0-L solvent reservoir was equipped with a nitrogen line and placed on a vertical support. Silica gel (4.8 kg) slurred in methylene chloride (12.0 L) was added to the column. Methylene chloride was drained from the bottom until the liquid level was just above the packed silica gel. Sea sand (1.5 kg) was added to the top of the reservoir.

(45) In a 5-L, round-bottom flask, crude product (Part 1—602.1 g; Part 2—588.8 g ) was dissolved in methylene chloride (2 L). This solution was gently poured onto the column. Methylene chloride (1 L) was used to rinse the 5-L round-bottom flask and the rinse was added to the column.

(46) A 2% methanol in methylene chloride solution (5×4 L) was gently poured, portion-wise, onto the column. The top pressure tube fitting was placed on the column, the column was pressurized with nitrogen and fractions (approximately 1 L) were collected.

(47) A 5% methanol in methylene chloride solutions (5×4 L) was gently poured, portion-wise, onto the column. The top pressure tub fitting was placed on the column, the column was pressurized with a nitrogen and fractions (approximately 1 L) were collected.

(48) All desired fractions (Par 1: fractions 20–42; Par 2: fractions 17–34) were drawn into the 20-L rotary evaporator bulb at a rate comparable to the rate of evaporation. Methylene chloride (50 mL) was used to rinse each fraction flask and the rinses were added to the rotary evaporator bulb.

(49) The crude product (Par 1 and Par 2 combined) as dried on a rotary evaporator for 18 hours at approximately 50° C.

(50) A 22-L, three-neck, round-bottom reactor in a heating mantle was fitted with a water-cooled condenser, an overhead stirrer system, and a six-inch powder funnel.

(51) Acetonitrile (2×4.0 L) was transferred to the rotary evaporator bulb (from Step 49) containing the crude product. The crude product was slurred in the acetonitrile.

(52) The suspension from Step 51 was transferred to the 22-L reactor and additional acetonitrile (1.0 L) was added. The mixture was headed to reflux until the solids dissolved (approximately 45 minutes).

(53) A 22-L, three-neck, round-bottom reactor was fitted with a gas inlet/outlet adapter and a Büchner™ funnel (186 mm) containing filter paper was placed in one of the necks. The remaining unused neck was closed with a glass stopper. The filtration apparatus was attached to a Gast® van vacuum pump.

(54) The vacuum pump was turned on. The filter paper was wetted with acetonitrile (100 mL), pressed in place, and coated with celite (200 g). After confirming a complete seal to the filter paper, the solution from Step 52 was filtered. Warm acetonitrile (333 mL) was used to rinse the celite pad. Additional acetonitrile (2×333 mL) was used to rinse the 22-L reactor and the rinses were used to rinse the filter cake.

(55) The 22-L reactor was placed in an ice/water bath and the Büchner™ funnel was replaced with an overhead stirring apparatus. Stirring was started and the solution was cooled to 3° C.–5° C. and held at that temperature for about 15 minutes.

(56) The contents of the 22-L reactor were vacuum filtered on a Büchner™ funnel (253-mm) through Sharkskin® filter paper [wetted with acetonitrile (100 mL)] into a 20-L glass carboy. The filter cake was washed with cold (less than 5° C.) acetonitrile (2×250 mL) followed by isopropyl acetate (2×250 mL). The filter cake was air dried until no further dripping from the tip of the funnel was observed.

(57) The filter cake was transferred to a 20-L Büchi rotary evaporator bulb. The filter cake was vacuum dried on a rotary evaporator using a Gast® van vacuum pump (greater than 25 inches Hg) at 50° C. for approximately 15 hours.

(58) The title compound was removed from the rotary evaporator, cooled to room temperature.

While the invention has been illustrated with respect to the production and use of particular compounds, it is apparent that variations and modifications of the invention can be made without departing from the spirit or scope of the invention.

Having thus described the invention, what is claimed is:

1. A method of forming a compound having the formula I

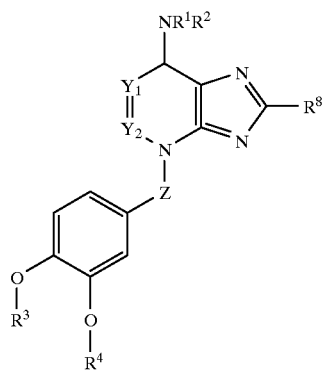

(I)

wherein:

$Y_1$ is N and $Y_2$ is CH

Z is $CH_2$;

$R^1$ and $R^2$ are independently selected from the group consisting of hydrogen and a $C_1$–$C_8$ straight or branched alkyl or a $C_3$–$C_8$ cycloalkyl;

$R^3$ is a $C_1$–$C_{12}$ straight or branched alkyl;

$R^4$ is a $C_3$–$C_{10}$ cycloalkyl optionally substituted with OH, or a $C_3$–$C_{10}$ cycloalkenyl optionally substituted with OH; and $R^8$ is a $C_1$–$C_8$ straight or branched alkyl or a $C_3$–$C_8$ cycloalkyl, optionally substituted with OH;

said method comprising the steps of;

(a) reacting a compound of the formula II

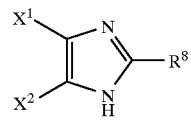

(II)

wherein $X^1$ is a carboxamide and $X^2$ is an amino group; with the benzaldehyde of compound (III)

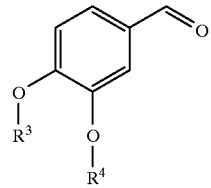

(III)

wherein $R^3$ and $R^4$ are as defined above;

followed by reduction of the resultant compound with a reducing agent to yield compound (IV)

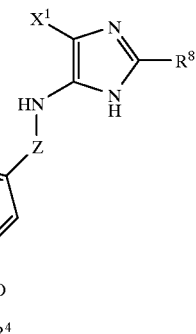

wherein Z, $X^1$, $R^3$, $R^4$ and $R^8$ are as defined above;

(b) reacting compound (IV) with triethylorthoformate to cause cyclization to compound (V) as set forth below

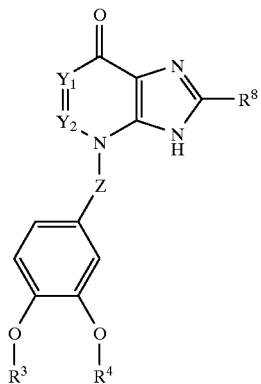

(V)

wherein $Y_1$, $Y_2$, Z, $R^3$, $R^4$ and $R^8$ are as defined above;

(c) transforming said compound (V) to an amine by successive halogenation with a halogenating agent and displacement of the resultant halogen with an amine of the formula $NR_1R_2$ wherein $R_1R_2$ are as defined above, to yield compound (I).

2. The method of claim 1 wherein said reaction with compound (III) occurs in the presence of an acid.

3. The method of claim 2 wherein said acid is selected from the group consisting of tosic acid or p-toluenesulfonic acid.

4. The method of claim 1 wherein said reducing agent is a borane anion.

5. The method of claim 1 wherein said ester is triethylorthoformate.

6. The method of claim 1, wherein said halogenating agent is a chlorinating agent.

7. The method of claim 1 wherein said compound of formula I is 3-(3-Cyclopentyloxy-4-methoxybenzyl)-6-ethylamino-8-isopropyl-3H-purine.

8. A method of forming a compound having the formula I

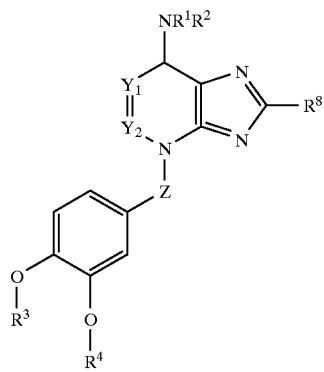

(I)

wherein:

$Y_1$ is N and $Y_2$ is CH

Z is $CH_2$;

$R^1$ and $R^2$ are independently selected from the group consisting of hydrogen and a $C_1$–$C_8$ straight or branched alkyl or a $C_3$–$C_8$ cycloalkyl;

$R^3$ is a $C_1$–$C_{12}$ straight or branched alkyl;

$R^4$ is a $C_3$–$C_{10}$ cycloalkyl optionally substituted with OH, or a $C_3$–$C_{10}$ cycloalkenyl optionally substituted with OH; and $R^8$ is a $C_1$–$C_8$ straight or branched alkyl or a $C_3$–$C_8$ cycloalkyl, optionally substituted with OH;

said method comprising the steps of;

(a) reacting a compound of the formula II

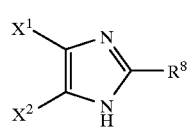

(II)

wherein $X^1$ is a carboxamide and $X^2$ is an halogen group; with compound (X)

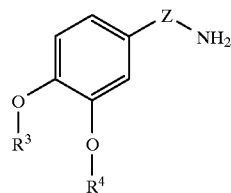

(X)

wherein $R^3$ and $R^4$ are as defined above, to yield compound (IV) as set forth below;

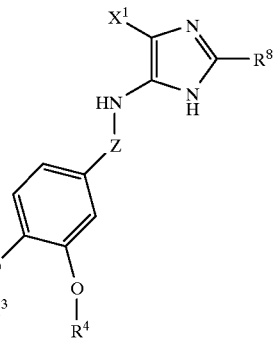

wherein Z, $X^1$, $R^3$, $R^4$ and $R^8$ are as defined above;

(b) reacting compound (IV) with triethylorthoformate to cause cyclization to compound (V) as set forth below

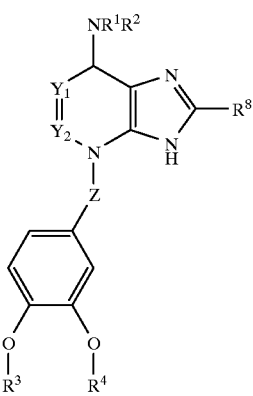

(V)

wherein $Y_1$, $Y_2$, Z, $R^3$, $R^4$ and $R^8$ are as defined above;

(c) transforming said compound (V) to an amine by successive halogenation with a halogenating agent and displacement of the resultant halogen with an amine of the formula $NR_1R_2$, wherein $R_1R_2$ are as defined above, to yield compound (I).

9. The method of claim 8 wherein $X^1$ and $X^2$ of compound (II) are bromide.

10. The method of claim 8, wherein said halogenating agent is a chlorinating agent.

11. The method of claim 8, wherein $R^1$ and $R^2$ are hydrogen; $R^8$ is isopropyl; $R^3$ is methyl and $R^4$ is cyclopentyl.

12. The method of claim 1, wherein $R^1$ and $R^2$ are hydrogen; $R^8$ is isopropyl; $R^3$ is methyl and $R^4$ is cyclopentyl.

* * * * *

UNITED STATES PATENT AND TRADEMARK OFFICE
CERTIFICATE OF CORRECTION

PATENT NO. : 6,211,367 B1
DATED : April 3, 2001
INVENTOR(S) : David J. Cavalla et al.

It is certified that error appears in the above-identified patent and that said Letters Patent is hereby corrected as shown below:

Title page,
Item [75], inventor names should read:
-- David J. Cavalla, Cambridge, Great Britain; Mark Chasin, Manalapan, New Jersey; Peter Hofer, Liestal, Switzerland; Harold Meckler, Delmar, New York; Chester J. Opalka, Averill Park, New York --

Signed and Sealed this

Ninth Day of April, 2002

Attest:

*Attesting Officer*

JAMES E. ROGAN
*Director of the United States Patent and Trademark Office*